United States Patent [19]

Giddings

[11] Patent Number: 5,039,426

[45] Date of Patent: * Aug. 13, 1991

[54] PROCESS FOR CONTINUOUS PARTICLE AND POLYMER SEPARATION IN SPLIT-FLOW THIN CELLS USING FLOW-DEPENDENT LIFT FORCES

[75] Inventor: John C. Giddings, Salt Lake City, Utah

[73] Assignee: University of Utah, Salt Lake City, Utah

[*] Notice: The portion of the term of this patent subsequent to Apr. 12, 2005 has been disclaimed.

[21] Appl. No.: 395,999

[22] Filed: Aug. 21, 1989

Related U.S. Application Data

[63] Continuation-in-part of Ser. No. 194,851, May 17, 1988, abandoned.

[51] Int. Cl.⁵ ............................................. B01D 35/06
[52] U.S. Cl. ......................................... 210/695; 209/12; 209/40; 209/127.1; 209/129; 209/131; 209/210; 209/422; 209/478; 209/493; 210/222; 210/243; 210/748; 210/800; 210/804
[58] Field of Search ............... 209/1, 2, 12, 18, 39, 209/40, 127.1, 129, 131, 132, 155, 156, 208, 210, 213, 214, 223.1, 232, 422, 478, 493, 494; 210/222, 223, 243, 695, 748, 800, 804

[56] References Cited

U.S. PATENT DOCUMENTS

| | | | |
|---|---|---|---|
| 4,102,780 | 7/1978 | Sun et al. | 209/213 |
| 4,235,710 | 11/1980 | Sun | 210/222 |
| 4,250,026 | 2/1981 | Giddings et al. | 209/156 |
| 4,663,029 | 5/1987 | Kelland et al. | 209/232 |
| 4,737,268 | 4/1988 | Giddings | 210/748 |
| 4,830,756 | 5/1989 | Giddings | 210/748 |
| 4,894,146 | 1/1990 | Giddings | 210/748 |
| 4,894,172 | 1/1990 | Williams | 210/748 |

FOREIGN PATENT DOCUMENTS 2317013 2/1977 France .............................. 210/695

Primary Examiner—W. Gary Jones
Attorney, Agent, or Firm—Terry M. Crellin

[57] ABSTRACT

A process for continuous particle and polymer separation comprising injecting a stream of carrier fluid containing the material to be separated into the inlet end of a thin channel, adjusting the flow rate to a sufficiently high level that flow-dependent lift forces the different components to different transverse positions by the time they reach the end of the channel, splitting the outlet flow into at least two substreams by means of physical splitters, adjusting the flowrates of the multiple substreams such that the transverse position of the outlet splitting plane divides the particles into enriched fractions, collecting the enriched or separated components from the emerging outlet streams.

16 Claims, 5 Drawing Sheets

PROCESS FOR CONTINUOUS PARTICLE AND POLYMER SEPARATION IN SPLIT-FLOW THIN CELLS USING FLOW-DEPENDENT LIFT FORCES

BACKGROUND OF THE INVENTION

This application is a continuation-in-part of my application Ser. No. 194,851, filed May 17, 1988, now abandoned

FIELD OF THE INVENTION

This invention relates to a new process for particle fractionation. More particularly, the invention relates to a new process for continuous particle separation in a split-flow thin cell using hydrodynamic lift forces.

Specifically, the invention provides a new and highly efficient process for the separation of particles, and particularly those having a size greater than 1 $\mu$m, which gives an unexpected increase in the resolution and speed of separation compared to known methods. The new process broadly comprises continuously injecting a stream of carrier fluid containing the material to be separated into the inlet end of a thin channel, adjusting the flowrate through the channel to a sufficiently high level that flow-dependent lift forces drive the different components to be separated to different transverse positions or distributions by the time they reach the end of the channel, splitting the outlet flow along the transverse axis into at least two substreams by means of physical splitters, adjusting the relative flowrates of the multiple substreams by external flow control means such that the transverse position of the outlet splitting plane divides the material into enriched fractions, and collecting the enriched or separated components from the emerging outlet streams.

The invention further provides a preferred embodiment wherein splitter means are employed at the inlet end of the channel.

The invention further provides another preferred embodiment wherein a primary external controlled driving force is applied transversely across the thin dimensions of the channel which force acts to drive the components transversely across the thin dimension of the channel and to assist the lift forces in establishing different positions or distributions for the different components to be separated.

As a further preferred embodiment, the invention provides a process as described in the preceding paragraph wherein the primary externally controlled driving force to be applied is a non-magnetic force so that the separation is in no way connected to the magnetic forces involved.

A further preferred embodiment comprises the combined process wherein both the inlet splitter means and the externally controlled driving force are employed to impart particularly outstanding results.

PRIOR ART

There is a growing need in industry and health sciences for the separation of particulate material whose components may incldue various kinds of macromolecules including DNA and synthetic polymers and micron sized particles including biological cells, latices, environmental partices, industrial powders, crystallization products, abrasives, etc.

Various methods have been proposed, but in general, they have been too slow, too low in throughput, inefficient, expensive or have failed to effect the separation with the desired degree of resolution.

Sun-U.S. Pat. No. 4,235,710 and Kelland, et al-U.S. Pat. No. 4,663,029 disclose methods for separation of particles but those techniques are based on the use of magnetic forces and are thus not suited for the separation of the larger number of particles not susceptible to such separation. In addition, such techniques are very slow as they are based on separation along the breadth coordinate extending from one side of the channel to another which is normally a distance of several centimeters or more.

Some of the highest resolution in the separation of particles has been obtained using two broad classes of techniques in which particle separation is achieved by controlling the transverse positions (or distributions) of particle populations within a thin (usually submillimeter) ribbon-like flow cell. In the first and best known of these classes, field-flow fractionation (FFF) as disclosed and claimed in U.S. Pat. No. 3,449,938 and U.S. Pat. No. 4,147,621, differences in mean transverse particle position are converted by the nonuniform (parabolic) flow in the channel into a differential migration rate along the longitudinal flow axis. A small injected sample pulse is thus separated along the flow axis and eluted as a sequence of component peaks. However, because FFF is a batch technique, the throughput is very small, usually one milligram or less.

In a more recently described class of techniques utilizing split-flow thin (SPLITT) cells as desclosed in U.S. Pat. No. 4,737,268, in copending patent application Ser. No. 067,487, filed June 29, 1987, and my article in Anal. Chem. 57 945 (1985), continuous separation is generated by taking direct advantages of the different transverse distributions (either equilibrium or non-equilibrium) of different particles across the thin dimension of the cell. In this case, separation is realized along the transverse axis rather than the flow axis as in FFF. The different particle components, each contained in its own flow stratum, are then divided by one or more flow splitters at the end of the cell and collected continuously in different outlet substreams. Because the process is continuous, the throughput is several orders of magnitude higher than in FFF.

Several kinds of transverse particle distributions can be established to implement these techniques. For FFF, where equilibrium distributions are generally employed, an exponential distribution at one wall (accumulation wall) is most commonly used. Separation is achieved by taking advantage of the different thicknesses of the exponential layers of different particles. However, since the exponential distributions strongly overlap along the transverse axis, the separation of such distributions by SPLITT methodology is limited.

Along several other possible approaches, different particle populations can be focused into individual thin bands or layers between the channel walls. These differentially elevated layers are termed hyperlayers. Although highly promising, hyperlayers are used very little in thin cell methods because of the difficulty of finding the proper combination of forces to tightly focus the particle populations into appropriate hyperlayers within the space available.

For both of the thin-cell methodologies, a wide variety of forces can be mobilized to manipulate, within certain limits, the transverse particle distributions. Many of the same primary (externally applied) forces can be used in the two classes of techniques, including sedimentation, electrical, temperature and crossflow forces.

In recent work disclosed and claimed in my copending patent application Ser. No. 155,774, filed Feb. 8, 1988, I have utilized forces of a substantially different nature, namely hydrodynamic (in large part inertial) lift forces, to help control the migration velocities of particles through field-flow fractionation channels.

It is an object of this invention to provide a process for utilizing these hydrodynamic lift forces for particles and similar lift forces for polymers in achieving separation in SPLITT cells as well.

SUMMARY OF THE INVENTION

It has now been discovered that this and other objects can be accomplished by the new process of the present invention which accomplishes a very rapid and efficient process for the separation of particles, particularly ultra high molecular weight polymers and micron sized particles, using the SPLITT cell process.

The process of the present invention comprises continuously injecting a stream of carrier fluid containing the material to be separated into the inlet end of a thin channel, adjusting the flowrate through the channel to a sufficiently high level that flow-dependent lift forces drive the different components to be separated to different transverse positions or distributions by the time they reach the end of the channel, splitting the outlet flow along the transverse axis into at least two substreams by means of physical splitters, adjusting the relative flow rates of the multiple substreams by external flow control means such that the transverse position of the outlet splitting plane divides the particles into enriched fractions, and collecting the enriched or separated components from the emerging outlet streams.

The invention further provides a preferred embodiment wherein splitter means are used at the inlet end of the channel, as well as an embodiment wherein a primary externally controlled driving force is applied which acts to drive the components transversely across the thin dimension of the channel and to assist the lift forces in establishing different positions or distributions for the different components to be separated.

The invention further provides a preferred embodiment wherein the primary externally applied driving force applied across the cell is a non-magnetic force so that the separation is in no way connected to the magnetic forces involved.

It has been surprisingly found that by the use of this new technique the lift forces can be readily employed in the SPLITT separation process to effect a rapid and highly efficient separation of particles and polymers, particularly polymers with molecular weights exceeding one million and particles with diameters greater than 1 μm.

Hydrodynamic lift forces acting on rigid particles were first described by Segre and Silberberg in J. Fluid Mech. 14 115 (1962). These forces differ in 2 major ways from the primary forces (sedimentation etc,) commonly applied across thin cells. First, the lift forces are highly nonuniform, exerting their greatest strength when particles are near the wall and dropping off rapidly as the particles penetrate more deeply into the interior of the channel. Second, the magnitude of the lift forces varies with flowrate. These two unusual features lead to different operating requirements and some unique opportunities in the application of these forces in thin cell methods.

Entropy-based forces acting on large polymeric molecules are also flow-dependent and highly nonuniform, and can similarly be used in this invention although they differ in many detailed respects from hydrodynamic lift forces. These forces were first described by Garner and Nisson, Nature 158 634 (1946). Similar lift forces can be assumed to act on deformable particles, which can be defined as particles capable of reversible changes in shape under mechanical or hydrodynamic stress.

For operational purposes we define lift forces generally as nonuniform, flowrate-dependent forces arising as a consequence of fluid motion and acting perpendicular to the direction of fluid flow.

Lift forces, as described above and used throughout this specification and claims, must be clearly distinquished from other forces commonly used in separations including viscous forces and gravitational forces. The latter forces not only fail to show a dependence on flowrate, they also tend to be uniform throughout the channel and they thus fail to provide the strongly nonuniform forces needed to realize this invention.

The nonuniformity of the lift forces makes it possible to combine these forces with uniform primary forces in order to develop component hyperlayers distributed at different transverse locations within the channel. This is illustrated for one component in FIG. 4 which shows the Force $F_L$ due to lift effects dropping off rapidly with distance x from the wall. A uniform force $F_1$ is applied in opposition to $F_L$: $F_1$ is shown as a negative quantity because it is directed along the negative x axis toward the accumulation wall. The sum of the two forces vanishes at position $x_{eq}$, which becomes the focus plane of the hyperlayer. Adjustments in the primary force $F_1$ can be used to shift the $x_{eq}$ value for different components to different positions to optimize the separation.

Hyperlayers cannot in general be formed by the superposition of uniform forces because the slope of the $F_1$ versus x plot, or the sum of such slopes, is essentially zero and cannot produce a zero force at a unique point. Lift forces, because of their non uniformity affords a unique means for generating hyperlayers.

The resolution of the SPLITT cell technique operating in the equilibrium hyperlayer mode is greatly improved if we impose two conditions. First, the equilibrium distance $x_{eq}$ of the hyperlayer from the wall must assume substantially different values for unlike particle species. Second, the hyperlayer of each particle population should be tightly forcused around the position $x_{eq}$.

In order to drive different kinds of particles to different hyperlayer positions (first criterion), one or both of the applied forces (primary and lift) must differ from one particle type to another. Based on recent work it now appears that both forces can be manipulated in order to increase the separation between hyperlayers.

The second condition requires that the focusing forces be rélatively large so that Brownian motion away from the equilibrium position is quickly subdued by strong restoring forces. High flowrates in thin channels generate strong lift forces near the walls. However, if no other forces are applied, particles are driven away from nearby wall elements where the lift forces (FIG. 4) and eventually lose much of their effectiveness. In order to maintain the strength of the lift forces, it is necessary to apply a conventional driving force to the system which acts in a direction opposite to that of the lift forces. With such a counteracting force the particles are driven vigorously toward the well defined transverse equilibrium position $x_{eq}$ shown in FIG. 4. With strong forces, particles of a given type will focus tightly around this equilibrium position to form a thin hyperlayer within the channel.

More specifically, the equilibrium position $x_{eq}$ of the above hyperlayer will be determined by the balance of forces condition $$F_1 + F_L = 0$$

where, as indicated in FIG. 1, $F_1$ is the externally applied primary force(s) and $F_L$ is the force due to lift effects. Since $F_1$ is generally subject to independent control, it can be increased to a relatively high absolute value which drives the particles closer to the wall. The magnitude of $F_L$ increases correspondingly as indicated by the above equation. Thus, within limits, the forces on a particle population can be controlled by external means and can be strengthened enough to ensure a tightly focused hyperlayer by the manipulation of this external control.

In the process of increasing the focus forces, the lift forces must be strong enough to maintain a force balance without the particles being driven into the wall or so close to the wall that wall interactions cause undue perturbations. Since the lift forces increase with flow velocity, substantial flowrates are necessary to maintain a functioning hyperlayer in the presence of large $F_1$ forces. Consequently, both high flow and high force conditions are necessary to optimize the resolution. However, in requiring high flow conditions we automatically establish favorable circumstances for high speed separation. For the SPLITT system, the high flowrates yield increased throughput.

It is possible to obtain separation in thin rectangular SPLITT cells by allowing different particles to approach different transverse equilibrium positions, that is, different values of $x_{eq}$. Two such populations can, in theory, be separated around the outlet flow splitter as shown in FIG. 5B. The particles are then collected from separate outlets.

Alternately, separation can be achieved on the basis of different rates of transport toward equilibrium. When particles are introduced in a thin laminae by means of a split inlet, they begin transport toward their respective equilibrium positions. Because of different transport velocities the different particles become transversely separated as they are driven toward their equilibrium position. If the channel length, fluid viscosity, and other factors are adjusted such that some of the particles reach the outlet splitter before approaching equilibrium, the different particle populations will be separated wholly or partially on the basis of different transport rates. Transport-based separation can be realized even when the equilibrium positions for different particles are almost the same, a condition applicable in most cases when an external or primary driving force is not used. More specifically, in the absence of a primary driving force, different particles are transversely separated because lift forces drive them at different transverse velocities. The separated particles can then be collected by approximately splitting the outlet flow.

As described above, the separation occurs along the transverse axis x, defined herein as the coordinate axis extending across the thin dimension of the channel between the two large closely spaced walls confining the channel volume. The shear rate and consequently the lift forces change very rapidly along this coordinate. As a result, separation is surprisingly made possible along the transverse axis even though the distance between the wall is often less than 1 or even ½ mm. Thus, the separated components may be spatially disengaged into distinct lamina only 1–200 μm apart, depending on conditions. While separation along such a short path, even if achievable, would normally be useless because the enriched fractions could not be readily divided from one another and collecteded, this division and collection is unexpectedly made possible by the channel configuration and the flow control described here. More specifically, the physical splitters are arranged in such a way that they divided the flow along the transverse axis. This means that the channel flow is split at some position $x_s'$, the position of the splitting plane, such that all stream laminae above $x_s'$ exit one outlet and all laminae below $x_s'$ exit another outlet (FIG. 6). In this way, the two divided substreams, each containing different components, can be individually collected.

We note that other continuous separation processes have been carried out in channels such as described by Giddings et al, Sun, and Kelland et al. However, the separations described by these authors take place along the breadth coordinate extending from one side of the channel to another, normally a distance of several centimeters or more. Such breadth coordinate separation are much slower than the transverse separations described here because of the greatly enlongated separation path. With equal driving forces, the separation time is roughly proportional to the separation path length, which may be one or two orders of magnitude longer for separations along the breadth axis. Even more significantly, the lift forces essential for the separation described herein cannot be utilized for separation over the breadth dimension of a thin channel. These forces are strong enough for separation only along gradients in the shear rate. These gradients are vanishingly small along most of the breadth axis of a thin channel. They act effectively only along the transverse axis.

The breadth-based separations described above utilize various kinds of collection ports or flow splitting to collect sample constituents. All of these devices collect fractions from different positions along the breadth coordinate, which, because of its larger scale, is a fairly straight forward task. Such splitting and sample collection configurations will not work for the transverse separation described here. The much more difficult task of splitting the flow to realize transverse separation is surprisingly achieved by the flow splitting process utilized in this invention.

As stated above, the transverse separation of the present invention is much more rapid than the breadth-based separation described above. Because of the high speed of the separation, the flowrate can be increased and thus the throughput can be made much larger than that achievable in a thin cell of the same cross sectional area where a breadth-based separation is carried out. Also the resolution of a transverse separation is surprisingly much higher than that of a breadth-based separation because in the former all particles having the same distance along separation path x, except for a few particles near the edges, will have the same velocity and the same lift forces so that they will be transported identically in the channel and emerge together well separated from particles having other characteristics. In a breadth-based separation, by contrast, particles found the same distance along the breadth coordinate will have a multitude of displacement velocities, ranging from 0 near the walls to 1.5 times of the average velocity at the midpoint of the channel. Thus, even identical particles are transported quite differently through breadth-based separation systems and resolution is thus lost.

Because we wish to fully utilize the uniformity in transport achievable along the transverse axis, the bulk of the separation cell, except in the splitter regions at the end, must not only be thin but it must be relatively simple, preferably confined by parallel wall elements. The channel must be free of obstructions and convoluted geometries like those described by Sun.

While primary driving forces might assist the transverse separation, they must be applied over the simple channel described above; they cannot be created by complicated and flow-disturbing pole pieces as described by Sun. Furthermore, the separation process described here cannot be achieved purely by the action of primary driving forces; the present invention utilizes in all cases the highly nonuniform properties of flow-dependent lift forces. This further distinguishes the present invention from that of Sun, Kelland et al, and Giddings et al, which not only describe breadth-based separations but can be utilized in the absence of lift forces.

DESCRIPTION OF THE DRAWINGS

The various objects and features of the present invention will be more fully understood by reference to the accompanying drawings.

With reference to FIG. 1, the thin elongated channel or cell is shown as 11 which comprises a top wall 12, bottom wall 13, inlet end 17 and outlet end 18, and spacer layers 14, 15 and 16 employed to create the desired channel volume.

With reference to FIG. 2 which is a side view of a thin channel, the physical splitter at the outlet end of the channel is shown as 19, the outlet ports as 20 and 21, and the inlet port as 22. The external force applied along the top of the channel is shown as 23.

FIG. 3 is a side view of a thin channel showing the physical splitters 24 and 25 at the outlet end of the channel with resulting outlet ports 26, 27 and 28, as well as a physical splitter 29 at the inlet end of the channel with inlet ports 30 and 31. The external force is shown as 23.

DETAILED DESCRIPTION OF THE INVENTION

Figure 1:
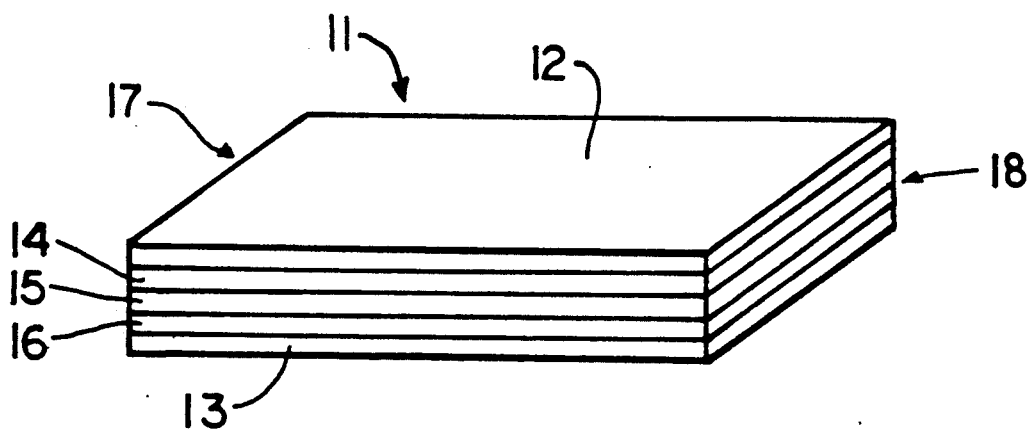
FIG. 1 is a perspective view of a thin elongated flow channel in this case constructed as a sandwich of individual spacer layers of a type which can be used in the process of the invention.
Figure 2:
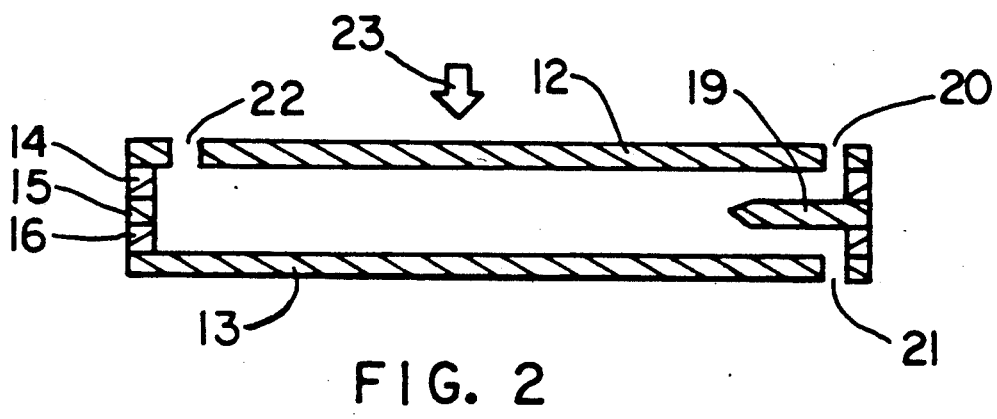
FIG. 2 is a side view of the channel showing the inlet and outlet ports and a physical splitter means.
Figure 3:
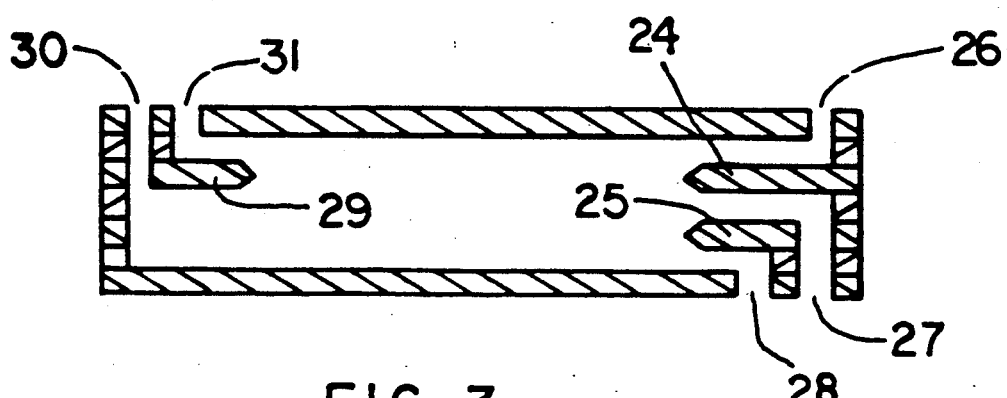
FIG. 3 is a side view of a channel showing the presence of two splitter means at the outlet end, and a physical splitter means at the inlet end of the channel.
Figure 4:
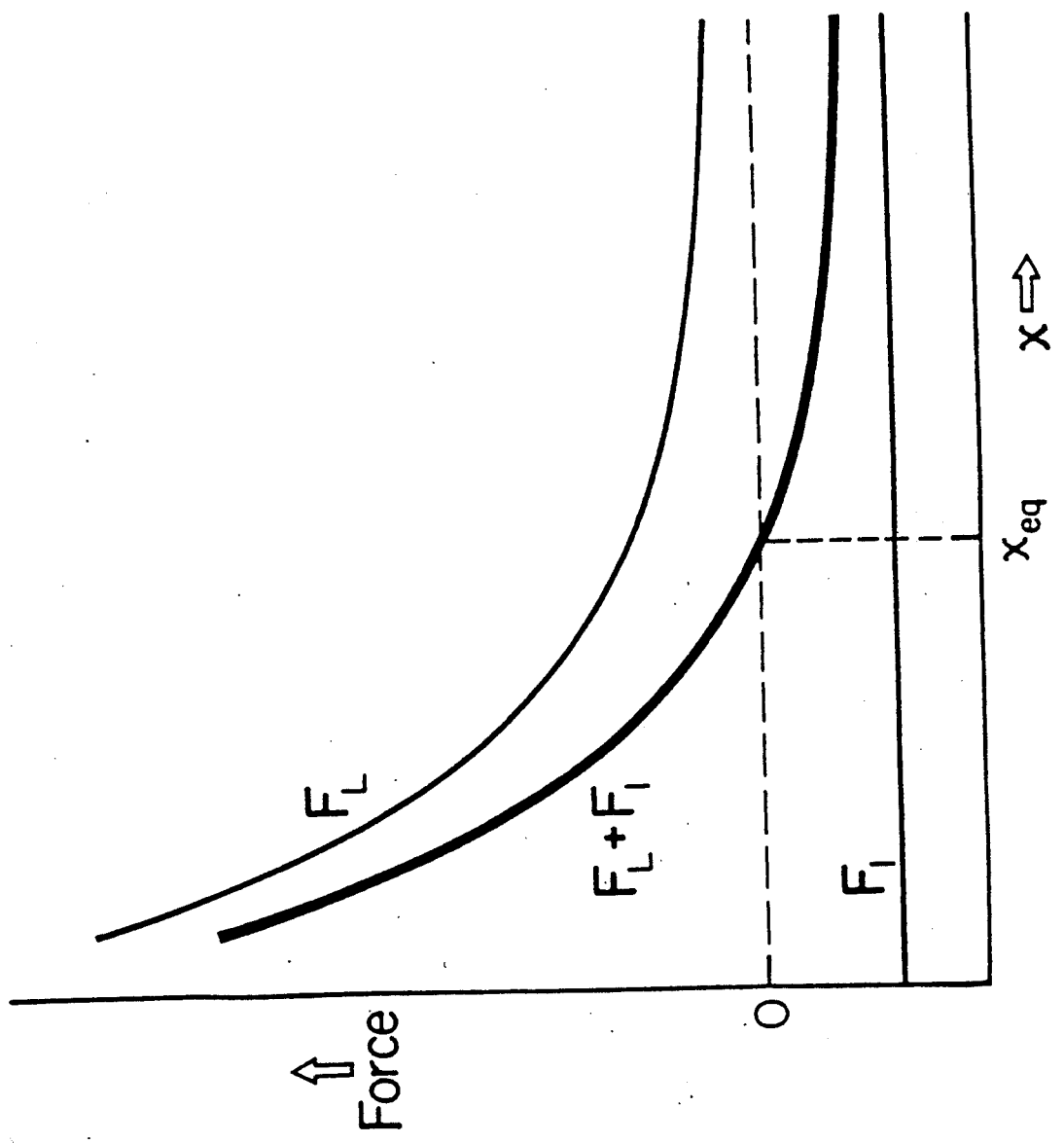
FIG. 4 is a graph plot of the forces exerted on a particle along the positive x-axis versus x, the distance from the channel wall. Since the force $F_L$ due to lift effects drops off rapidly with distance x, it can be combined with an opposing uniform force $F_1$ to establish a position $x_{eq}$ of zero net force, around which a hyperlayer will accumulate.
Figure 5A:
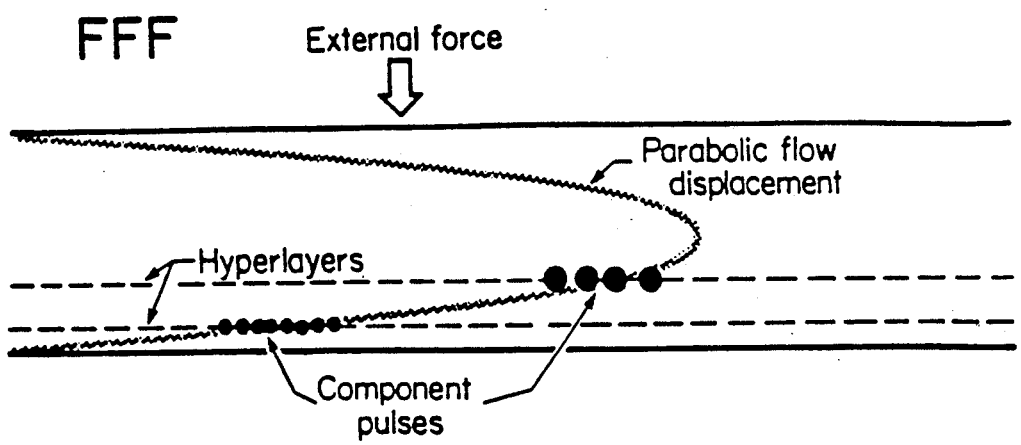
FIG. 5A and 5B are diagramic illustrations of a side view of a channel showing the contrast between hyperlayer separations in FFF systems and in SPLITT cells. In hyperlayer FFF a sample pulse first divides into hyperlayers and then separates along the flow axis by virture of the parabolic flow profile. In hyperlayer SPLITT operation, a continuous sample stream divides into component hyperlayers which are then separated along the transverse axis by a stream splitter.
Figure 5B:
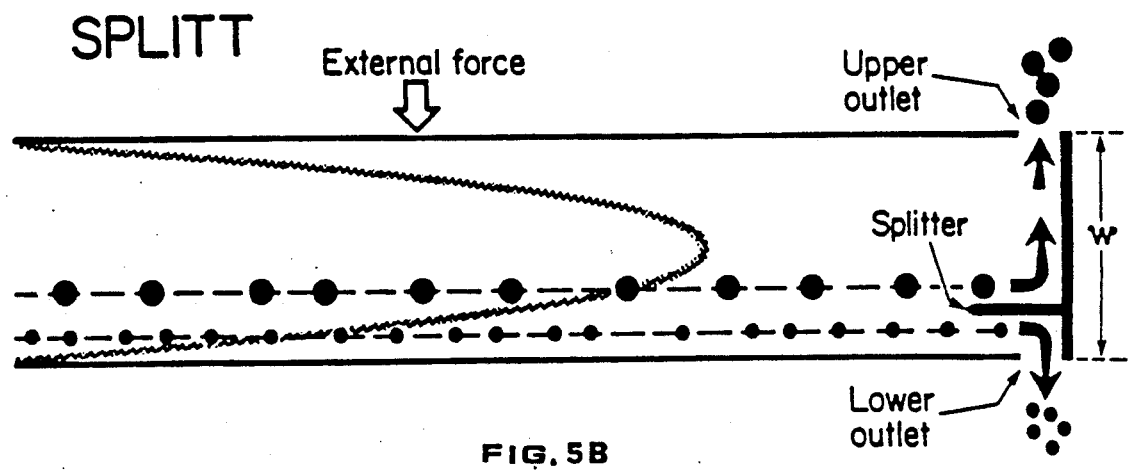

The type and size of the various types of particles to be separated can vary over a wide range depending on flow conditions, type and strength of field, etc. The particles can be as small as 0.5 $\mu$m or larger than biological cells. Preferably, the particles range in size from about 1 $\mu$m to 100 $\mu$m. The particles can also vary as to density and shape, and the conditions of the separation process will be adjusted accordingly. For polymers, the preferred molecular weight is one million or more.

The particles to be separated include biological cells, latices, environmental particles, powders and the like. A preferred group of particles include rigid particles, such as silica particles and particles of abrasive powders. Other preferred particles include deformable particles, such as red blood cells, liposomes, and emulsions. Preferred molecules or macromolecules include DNA, polysaccharides, and synthetic water soluble and organic soluble polymers of high molecular weight. The process can be utilized for the separation of the same type of particles or mixtures of various types can be utilized. Alternately, preferred particles can be separated from smaller particles for which lift forces are negligible.

The carrier fluid in which the particles are to be separated may also vary over a wide range of properties. In most cases, the fluid will be that in which the particles are normally prepared or contained, such as aqueous buffers for biological particles. In other cases, the carrier consists of specially prepared fluids or solutions in which the density, viscosity or other fluid characteristic is controlled in order to optimize the separation.

The concentration of the particles in the incoming particle-containing substream can also vary widely from extreme dilutions up to about 30% or more. In most cases, the concentration will vary from about 0.1% to about 10% by weight.

The external driving force preferably employed in the process include those forces or gradients which effect transverse movement of the particles. In operation, a component of such force or gradient is applied perpendicular to the plane of the stream flow, i.e. along the transverse axis. The forces and gradients include, among others, sedimentation forces, such as caused by gravitation and centrifugation, electrical, dielectrical, cross flow, temperature gradient force, and combinations thereof. Preferred forces include sedimentation forces, cross flow gradients, electric and temperature gradient forces.

As noted, a preferred embodiment of the invention involves the use of non-magnetic forces so that such are not involved in the separation process.

The strength of the force to be applied to the channel varies depending on several factors, such as particle mobility, thickness of separation cell, fluid density, etc, and is best determined for each individual case. As noted above, the force is primarily used in conjunction with the flow dependent lift forces to establish different equilibrium hyperlayer positions for the different components to be separated.

The temperature employed in the separation process can vary over a wide range, but generally will range from about 0° C. to 35° C., with ambient temperature being preferred.

The rate of introducing the fluid containing the particles may vary as needed. As noted the total flowrate is adjusted to a sufficiently high level that flow-dependent lift forces drive the different components to be separated to different positions, and is further adjusted in relationship to the channel length and thickness and the carrier viscosity such that the components to be separated are made to approach their respective equilibrium positions to within the desired degree, or prevented from approaching equilibrium in other cases, while still in the channel.

Such adjustment is accomplished by external pump means. When a split inlet is used, both incoming flow streams are controlled independently by pump means.

When using a split inlet, increasing the flowrate of the sample substream a' increases throughput but decreases resolution. Thus relative inlet flowrates must be established by compromise.

The flowrate can also be further adjusted in relationship to the channel length and thickness and the carrier viscosity such that the components to be separated approach different positions before reaching the end of the channel. The channel length and thickness has the effect of influencing the closeness of the approach to equilibrium. The channel thickness, particularly, affects transport rates at a given flowrate and thus affects closeness to equilibrium.

The carrier viscosity has the effect of reducing transport rates but in some circumstances, as with polymers, it also increases the lift driving forces. Therefore, in some cases viscosity can be changed to influence the degree of transport and the approach to equilibrium.

As noted the channel stream is split at the outlet end into at least two substreams by means of physical splitters. Such splitter means at the outlet, and sometimes at the inlet end can be of any desired shape and size as long as they accomplish the purpose of splitting the channel stream into physical distinct laminae.

As noted hereinabove, the generic expression "splitter means" refers to all such means, including especially placed outlet ports, physical barriers, and the like. The expression "physical" splitter as used herein refers to the actual physical barrier as shown in FIG. 1.

The preferred physical splitters are preferably prepared from very thin material, such as plastic or metal sheeting and extend preferably only a short distance into the cell, e.g. 1 to 5 cm. They preferably extend through the tapered or triangular end regions of the cell so as to facilitate a clean separation of laminae.

As noted, the relative flowrates of the multiple substreams are adjusted as by external flow control means such that the transverse position of the outlet splitting plane lies between that of the components to be separated.

As used herein "splitting planes" refers to boundary planes between laminae that are produced by different substreams or that will form different outlet substreams. The splitting planes coincide with very specific streamplanes of fluid flow. The inlet splitting plane follows the streamlines dividing the laminae formed by merger of two inlet substreams. The splitting planes may swerve up or down near the edges of the channel splitters. These deflections are transient, resulting from the brief transition from one steady-state flow condition to another near the splitters edges.

The particle fractions obtained by the above-noted process will be recovered at the various outlet means in the form of fluid solutions or suspensions, which may be used directly as such or which may be subjected to further separation means, such as by centrifugation or evaporation, to recover the particles themselves.

The apparatus to be used in the process of the invention can be constructed in a variety of ways with a variety of different materials and sizes as long as it provides the desired thin channel or cell, the desired number of inlet and outlet means, the desired splitter means, pumping means, flow control means and means for applying the preferred external driving force.

The thickness of the channel is an important feature of the invention. The thickness of the channel along which dimension the separation takes place must be very thin compared to the other two dimensions, and preferably less than five millimeters. Particularly good results are obtained when the thickness varies from about 0.1 mm to about 4 millimeters, and still more preferably from about 0.2 mm to about 2 mm.

The length and breadth of the channel may vary over a wide range as long as these dimensions are considerably greater than the thickness noted above. Increasing the length and breadth is desirable to increase throughput.

The channel should possess at least one inlet means for introducing the fluid substream containing the particles to be separated. Such means, which may be ports or holes may be located at the top of the inlet end or at the front end of the separation cell as desired for the creation of the necessary substreams.

The channel in some cases also has a split inlet with two inlet means for introducing a particle-free substream. These means, which also may be ports or holes may be located at the bottom of the inlet end or at the end of the separation cell as desired for the creation of the desired substream. As noted, pump means may be employed manually or automatically to assist in the injection at the said inlet means. Splitter means can also be used at the inlet end to split the flow into two or more substreams as desired.

While the process may be described as separation of two particle populations, it is not limited to only two components. In parallel with other forms of SPLITT cell operation, one can increase the number of fractions separated either by using multiple outlet splitters to divide the flow into a number of outlet substreams, each with its own component or fraction, or by linking cells together in such a way that the outlet substreams from the first cell enter subsequent cells for additional fractionation steps.

It is also noted that if the hyperlayers are crowded into a limited fraction of the channel cross section, the splitter need not be located in that limited region in order to divide the hyperlayers. Instead, the splitter can be placed at some more convenient location, often at a position half-way across the channel. To split the flow at some off-center position, we need only adjust the flow rates (specifically in this case the two outlet flowrates) so that each outlet stream carries a specified fraction of the total flow. This is explained as follows.

Figure 6:
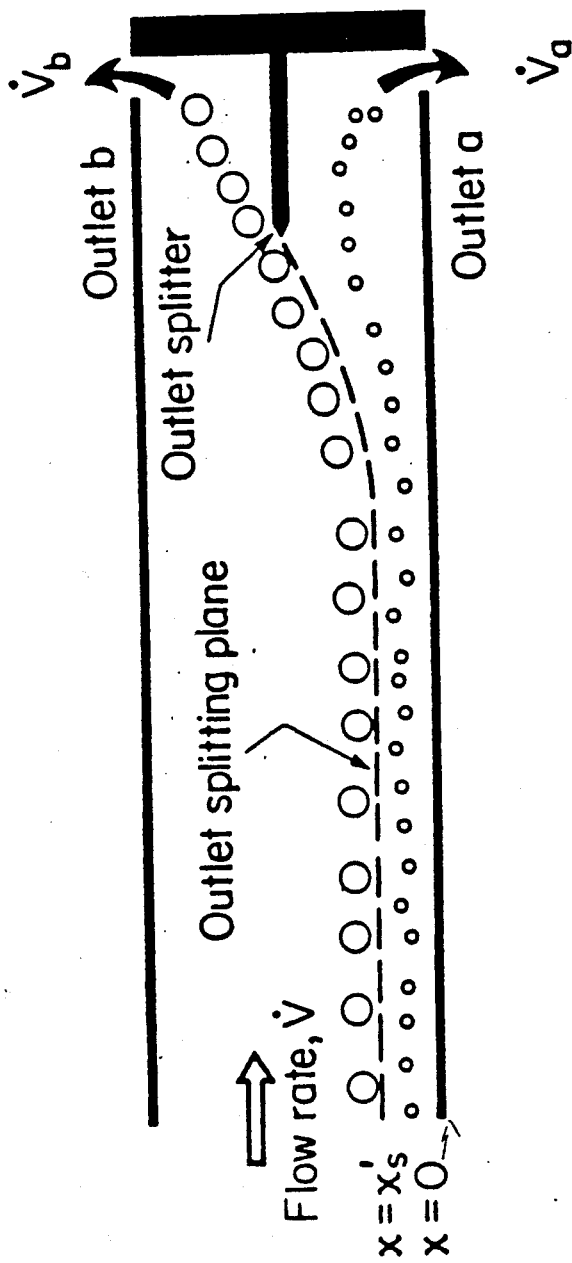
FIG. 6 is a diagramic illustration showing the relationship of outlet splitting plane and outlet splitter. In that Figure, $V_b$ and $V_a$ represent the flow rate of the fractions at the outlet end of the channel, and V the total flow rate of the material being introduced at the inlet end of the channel.
Figure 7:
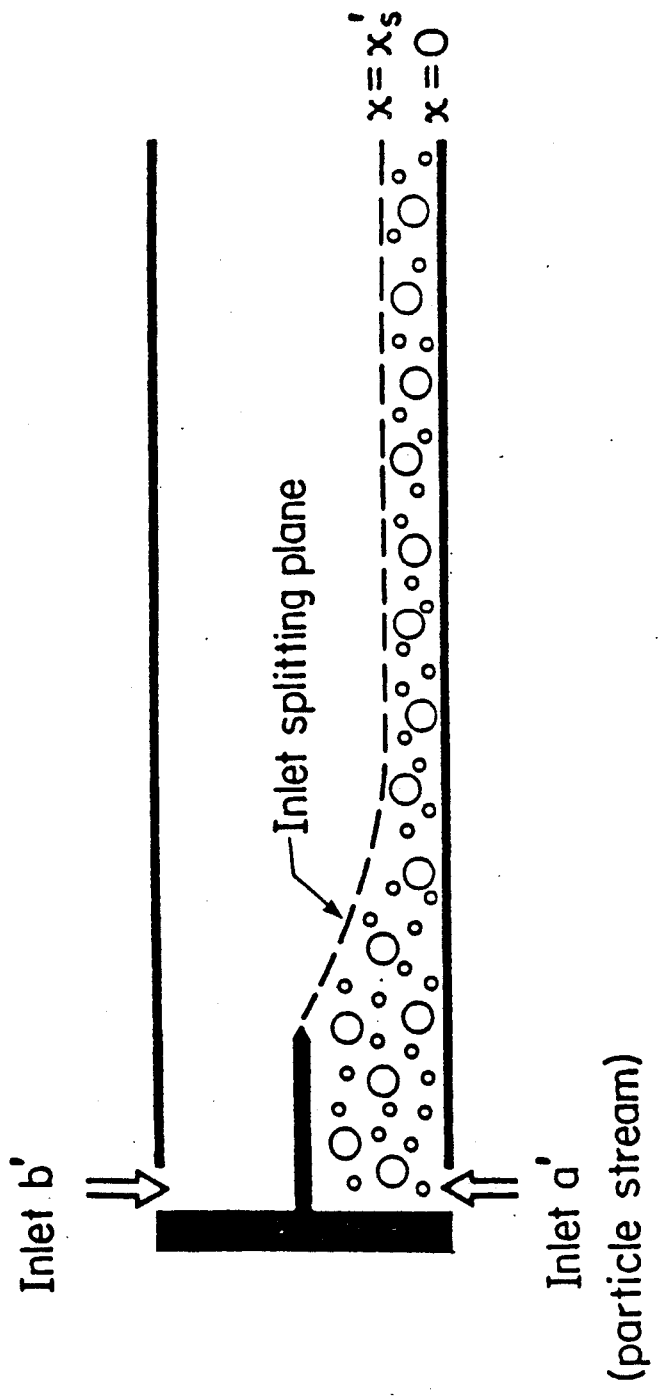

For any given ratio of outlet flows, an outlet splitting plane can identified running back into the channel from the edge of the splitter to the cell inlet region. We define a splitting plane as a plane dividing two adjacent flow laminae in the cell; it is thus a plane across which no fluid is transported by flow. Providing the flow conditions remain laminar, all the fluid above the outlet splitting plane will exit outlet b and all that below, outlet a. While the downstream edge of the outlet splitting plane will, by definition, always be anchored to the outlet splitter as shown in FIG. 6, the steady-state position of the splitting plane through most of the channel will be determined by the ratio of the volumetric flowrates above and below the splitting plane, a ratio controlled by the two outlet flowrates.

While the above process is likely to be most easily implemented with particles suspended in liquids where the lift forces are substantial it is also applicable to particles suspended in air at sufficiently high flowrates.

SPECIFIC EMBODIMENT OF THE INVENTION

A specific embodiment of the new process of the invention and illustration of its use are illustrated below.

Split-flow thin (SPLITT) separation cells were constructed by sandwiching three spacer layers between glass plates. Each of the outer layers was a 102-$\mu$m thick Teflon sheet with a portion cut and removed to provide part of the cell volume. The sections removed had a length of 14 cm and a breadth of 2 cm. The center spacer, a 127-$\mu$m thick stainless steel sheet, also had a section of 2-cm breadth removed but this section was shorter, allowing the stainless steel sheet to extend into the separation cell to form the physical splitters at the two ends.

Two such cells were utilized, one in which the distance between the splitter edges was 2 cm and the other 10 cm. The three-layer channel structure, after being sandwiched between glass plates, was bolted together with plexiglass clamping bars. The channel assembly was then set on end so that the flow axis was vertical and gravitation would not contribute to the transverse driving force. The flow through the cell was controlled by three laboratory pumps.

The operation of the SPLITT cell was tested using suspensions of 10—, 20—, 30— and 50 $\mu$m polystyrene latex beads. The suspending medium used to transport the latex through the channel was water containing 0.1% FL-70 detergent and 0.02% sodium azide. The emerging particles were counted with a microscope and a hemocytometer.

The shorter 2-cm cell was found to be most suitable for separation of the larger particles but of inadequate length for the smaller particles. A 0.2% suspension of 30— and 50-$\mu$m beads was introduced into the cell at inlet a' as feed material. The flowrate of the feed stream was V=0.19 mL/min while the flowrate of the pure carrier stream was $V_a \mp 8.00$ mL/min giving a total flowrate through the cell of 8.19 mL/min. The flowrates at the two outlets were $V_b=0.65$ mL/min and $V_b=7.54$ mL/min. The liquid suspension emerging from the two outlets was collected and subjected to microscopic examination.

For the mixture of 30— and 50-$\mu$m latex feed the number ratio of 30-$\mu$m to 50-$\mu$m particles was measured as 3.4. In the a outlet this ratio was increased to 167, which represents a 49-fold enrichment of the 30-$\mu$m particles. For the b outlet this ratio was at the opposite extreme, 0.06, representing nearly complete removal of the 30-$\mu$m particles from the 50-$\mu$m population. The enrichment of the 50-$\mu$m latex was over 56-fold.

The longer 10-cm cell was used to fractionate the 10— and 20-$\mu$m latex mixture. The outlet flowrates in this case were adjsted to $V_a=0.40$ mL/min and $V_b=7.79$ mL/min. The number of 10-$\mu$m relative to 20-$\mu$m latex beads in the feed was 2.6. Microscopic observations showed that this ratio had increased to 412 at the a outlet, representing an enrichment of 10-$\mu$m particles of over 150. The ratio dropped to 0.13 at the b outlet, representing a 20-fold enrichment of the 20-$\mu$m particles.

Since gravitational forces were made negligible in these experiments by the vertical orientation of the cell and since no other forces were acting on the particles, these experiments prove that hydrodynamic lift forces can be successfully used to separate particles with diameter $>1$ $\mu$m.

I claim as my invention:

1. A process for continuously separating components of particulate and macromolecular materials comprising introducing a continuous stream of carrier fluid containing such materials into an inlet end of a separation cell comprising a thin channel whose thin dimension is less than 5 mm and whose breadth and length are at least about 2 cm, adjusting flowrate of said stream through the channel to a sufficiently high level that flow-dependent lift forces drive different components to be separated to different transverse positions or distributions across the thin dimension of the channel by the time they reach an outlet end of the channel, splitting outlet flow from the outlet end along a plane transverse of a coordinate axis extending across the thin dimension of said channel to divide the outlet flow into at least two substreams by means of physical splitters, and adjusting relative flowrates of the substreams by external flow control means such that the materials are divided into enriched fractions in the substreams.

2. A process as in claim 1 wherein a physical splitter is used to divide the inlet end of the channel into first and second inlet passages on opposite sides of a plane transverse of a coordinate axis extending across the thin dimension of said channel, with the stream containing the material to be separated being introduced in the first inlet passage and another stream not containing the material being introduced into the second inlet passage.

3. A process as in claim 1 wherein an externally controlled driving force is applied across the thin dimension of the channel, said driving force acting to drive the components transversely across the thin dimension of the channel to assist the lift forces in driving the different components to different transverse positions across the thin dimension of the channel.

4. A process as in claim 3 wherein a physical splitter is used to divide the inlet end of the channel into first and second inlet passages along a plane transverse of a coordinate axis extending across the thin dimension of said channel, with the stream containing the material to be separated being introduced in the first passage and another stream not containing the material being introduced into the second inlet passage.

5. A process as in claims 1, 2, 3, or 4 wherein there are at least two splitters for splitting the outlet flow into at least three substreams to provide for the separation of at least three or more fractions.

6. A process as in claims 1, 2, 3, or 4 wherein at least one of the substreams emerging from said channel are fed to a subsequent channel similar to said channel where further fractionation takes place.

7. A process as in claims 1, 2, 3 or 4 wherein the cell thickness is less than 2 mm.

8. A process as in claims 1, 2, 3 or 4 wherein the external driving force consists of a member of the group consisting of sedimentation force, an electrical force, a dielectrical force, a magnetic force, a temperature gradient force, and combinations thereof.

9. A process as in claims 1, 2, 3 or 4 wherein the driving force consists of the cross flow of fluid transversely across the separation cell.

10. A process as in claims 1, 2, 3, or 4 wherein the particles are continuously distributed with respect to size and in which the splitters at the outlet end of the channel are positioned to split the outlet flow in such a way that each substream has material having a designated size range different from that found in any other substream.

11. A process as in claims 1, 2, 3 or 4 wherein the material to be separated consists of rigid particles.

12. A process as in claims 1, 2, 3 or 4 wherein the material to be separated consists at least in part of deformable particles.

13. A process as in claims 1, 2, 3 or 4 wherein the material to be separated consists of biological cells.

14. A process as in claims 1, 2, 3 or 4 wherein the material to be separated consists of different macromolecular components.

15. A process as in claims 1, 2, 3 or 4 wherein the material to be separated consists of a mixture of rigid particles and deformable particles.

16. A process as in claims 1, 2, 3 or 4 wherein at least one of the components to be separated does not approach its equilibrium hyperlayer position prior to stream splitting at the outlet end.

* * * * *